US006825467B2

(12) United States Patent
Drown et al.

(10) Patent No.: US 6,825,467 B2
(45) Date of Patent: Nov. 30, 2004

(54) APPARATUS FOR SCANNING A CRYSTALLINE SAMPLE AND ASSOCIATED METHODS

(75) Inventors: Jennifer Lynn Drown, Orlando, FL (US); Kim Elshot, Winter Park, FL (US); Erik Cho Houge, Orlando, FL (US); Terri Lynn Shofner, North Plains, OR (US); Tingkwan Cheung, Singapore (SG)

(73) Assignee: Agere Systems, Inc., Allentown, PA (US)

( * ) Notice: Subject to any disclaimer, the term of this patent is extended or adjusted under 35 U.S.C. 154(b) by 202 days.

(21) Appl. No.: 10/180,221

(22) Filed: Jun. 25, 2002

(65) Prior Publication Data

US 2003/0234359 A1 Dec. 25, 2003

(51) Int. Cl.[7] .......................................... G01N 23/203
(52) U.S. Cl. ..................... 250/307; 250/306; 250/310
(58) Field of Search ................................ 250/307, 306, 250/310, 311

(56) References Cited

U.S. PATENT DOCUMENTS 5,350,921 A * 9/1994 Aoyama et al. ............ 250/311
5,744,800 A * 4/1998 Kakibayashi et al. ....... 250/311
6,326,619 B1 * 12/2001 Michael et al. ............. 250/310
6,411,906 B1   6/2002 Goto

OTHER PUBLICATIONS

George Vander Voort, *Committee E–4 and Grain Size Measurements: 75 Years of Progress*, ASTM Standardization News, May 1991, USA.

* cited by examiner

Primary Examiner—Kiet T. Nguyen

(57) ABSTRACT

The present invention provides and apparatus and method for scanning a crystalline sample comprising a sample holder, an electron source for generating an electron beam and a scanning actuator for controlling the relative movement between the electron beam and the crystalline sample. In addition, an image processor is provided for processing images from electrons from the crystalline sample and a controller for controlling the scanning actuator to space points on the crystalline sample, at which the electron beam is directed. The points are preferably spaced apart a distance that is at least as large as a known grain size of the crystalline sample. The controller determines a grain orientation with respect to each point within a series of points within a scan area of the crystalline sample. The controller determines an average grain orientation for the crystalline sample for current image and a previously processed image. The controller monitors a variance in the average deviation and terminates the scanning when the variance in the average grain orientation approaches a predetermined value.

17 Claims, 4 Drawing Sheets

APPARATUS FOR SCANNING A CRYSTALLINE SAMPLE AND ASSOCIATED METHODS

FIELD OF THE INVENTION

The present invention relates to the field of materials analysis and, more particularly, to analyzing the grain structure of crystalline materials.

BACKGROUND OF THE INVENTION

The complexity of the preferred orientation of polycrystalline microstructures has increasing significance within many industrialized fields. This microstructure can be examined with a variety of techniques. Multiphase two-dimensional mapping of crystallographic and morphological data provides challenges to determine the crystallographic grain orientation, grain size and grain boundaries of a crystalline sample. There are numerous ways of obtaining this information, but each of the methods presents slightly different information that the others do not.

The processing of materials in the semiconductor industry to achieve smaller geometries introduces new problems as the boundaries between grain structures and the orientations of the boundaries become more critical. For example, the conventional method of indexing Kikuchi diffraction patterns over a scanned area is one method of determining both the crystallographic orientation and grain morphology of thin films on sample surfaces. Backscattering Kikuchi Diffraction (BKD) in a scanning electron microscope can produce Kikuchi bands from polycrystalline grains approaching the size of the probe diameter. By applying the rules of point group symmetry to the Kikuchi bands, characteristics such as crystallographic grain orientation and grain size within a specimen can be determined.

Grains within polycrystalline materials generally have orientations that vary from grain to grain. This variation, when considered over a bulk specimen area, can lead to the directional grouping of specific crystalline planes with respect to certain crystallographic axes. The "preferred orientation" of a polycrystalline sample refers to an average, or overall, orientation of the grains. The complexity of the preferred orientation of polycrystalline microstructures can be examined with a technique known as Orientation Imaging Microscopy, which analyzes collections of BKD patterns. This technique combines the advantages of point orientation in Transmission Electron Microscopy (TEM) with morphological information over a large enough area to provide statistical relevance.

Aluminum deposited by chemical vapor deposition (CVD) deposits in a preferred orientation along a (1,1,1) fiber texture normal to a silicon substrate. This geometry is preferred to reduce electromigration. BKD pattern analysis can be used to quantify the quality of the deposition of the aluminum along the preferential crystallographic axis.

The movement of the semiconductor industry to copper metallization will require seed layers and barrier layers made out of tantalum nitride, for example. The deposition of copper by CVD does not seem to exhibit preferential orientation. This results in a variable that can differ between deposited copper films. BKD analysis provides a way of quantifying the films for orientation analysis in a two-dimensional mapping array whereby the preferred grain orientations can be compared from one film to another.

BKD pattern analysis works by collecting a Kikuchi pattern at a specific location on a sample surface, converting the pattern to a Hough space where each line is represented as a spot, and using the angular deviations between the spots to calculate the crystallographic orientation of the crystal at that location. The scanning electron microscope beam or the sample stage is then stepped to the next point and the process is repeated. The stepping occurs in a raster pattern with a fixed step size over the entire scan area. Unfortunately, this method is very time consuming. For example, to acquire a pattern from an area that is 10 square micrometers with a step size of 50 nm, approximately 40,000 individual Kikuchi patterns must be collected and analyzed. With each Kikuchi pattern typically taking approximately 0.5 seconds, this yields a scan time for the entire area of approximately 11 hours.

The pattern also has a maximum grain boundary resolution of 50 nm. The lengthy collection time of these patterns makes automated BKD pattern analysis labor intensive and time consuming. Increasing the step size does decrease the time element involved in obtaining and analyzing date with respect to certain characteristics of a polycrystalline material.

The foregoing metrological techniques are conducted off-line, i.e., by taking partially fabricated structures in fabrication, including semiconductor devices, out of the manufacturing sequence. However, inline metrology techniques that identify either grain size or preferred orientation of polycrystalline films do not exist. Semiconductor devices are typically destructively measured offline by time consuming techniques of electron diffraction and x-ray diffraction. The disadvantage of these offline techniques is that they require constant monitoring on test structures and wafers, which results in a window between when problems occur and when problems are detected.

SUMMARY OF THE INVENTION

The present invention provides an apparatus for scanning a crystalline sample, including a sample holder, an electron source for generating an electron beam, and a scanning actuator for controlling relative movement between the electron beam and the crystalline sample. The scanning actuator is preferably controllable for directing the electron beam at a series of spaced apart points of the crystalline sample. Moreover, the apparatus also preferably includes an image processor for processing an image based upon electrons from the crystalline sample, and a controller for controlling the scanning actuator to maintain a distance between the points such that each image processed is representative of a different grain of the crystalline sample. Accordingly, the number of points required by the present invention may be significantly less than the number of points required for conventional fixed spaced systems, thereby significantly reducing the time for scanning the crystalline sample.

The image is preferably a Kikuchi diffraction pattern. The sample holder preferably holds the crystalline sample in a substantially horizontal position. The electron source is positioned such that an electron beam generated therefrom is at an angle approximately 20° above horizontal. Furthermore, the apparatus preferably includes a phospor screen adjacent the sample holder, at a right angle incident to the electron beam, for forming the image defined by the electrons from the crystalline sample. The image processor may include a low light camera or a CCD camera for capturing the image defined by electrons from the crystalline sample. Also, the image processor may convert the Kikuchi diffraction pattern to a Hough space to identify Kikuchi bands at a point within the crystalline sample. The image processor may determine a crystallographic grain orientation at the point within the crystalline sample based on the Kikuchi bands. The controller determines an average crystallographic grain orientation for the crystalline sample from the processed images, and monitors any variance in the average grain orientation during the scanning of the crystalline. When the variance in the average grain orientation approaches a predetermined value, the scanning of the crystalline sample is terminated.

The objects, features and advantages in accordance with the present invention are provided by a method including the steps of providing the crystalline sample, generating an electron beam, and controlling relative movement between the electron beam and the crystalline sample to direct the electron beam at a series of spaced apart points of the crystalline sample. Furthermore, an image based upon electrons from the crystalline sample is processed, and a spacing between points is maintained so that each point is representative of a different grain of the crystalline sample.

In a preferred embodiment, the present invention is integrated in the fabrication process of semiconductors as an in-line method of scanning the crystalline materials. The present invention provides a means of testing the quality of device films real time, to identify problems during the manufacture of integrated circuits. An ability to monitor the metrology and/or morphology of the crystalline specimens "in-line" enables one to identify issues "in-line", and extend the quality of the product, reduce scrap while increasing yield of a product.

DETAILED DESCRIPTION OF THE PREFERRED EMBODIMENTS

The present invention will now be described more fully with reference to the accompanying drawings, in which exemplary embodiments of the invention are shown. This invention may, however, be embodied in many other forms and should not be construed as limited to the disclosed embodiments. Rather, these embodiments are provided so that this disclosure will be thorough and complete, and will fully convey the scope of the invention to those skilled in the arts. Like numbers refer to like elements throughout.

Figure 1:
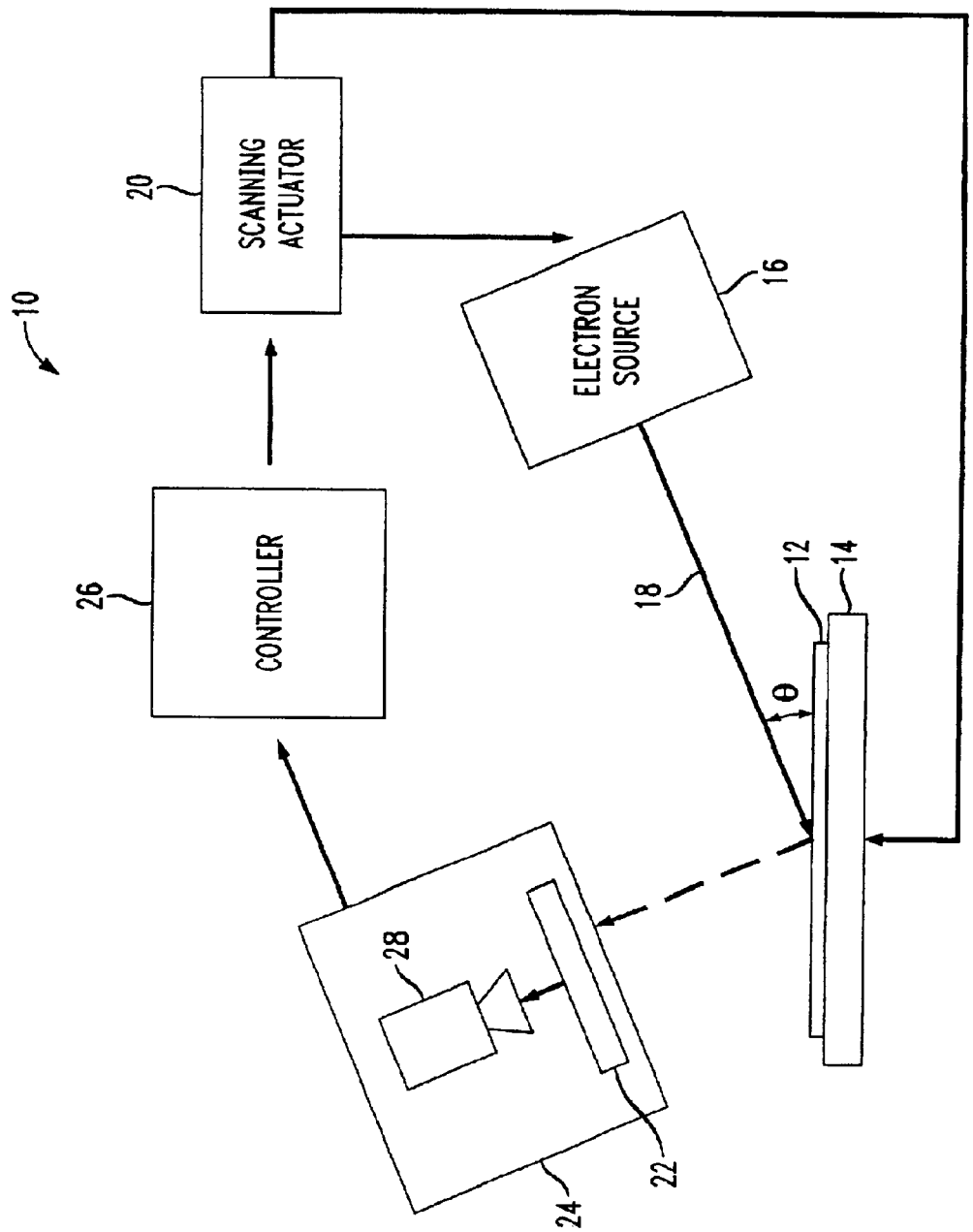
FIG. 1 is a schematic view of an apparatus in accordance with the present invention.

Referring to FIG. 1, an apparatus 10 for scanning a crystalline sample 12, such as a copper film deposited on a semiconductor wafer, will now be described. The apparatus 10 includes a sample holder 14 for holding the sample 12 at a glancing angle θ to an electron beam 18. The electron beam 18 is generated by an electron source 16. A scanning actuator 20 is provided for controlling relative movement between the electron beam 18 and the crystalline sample 12 on the sample holder 14. The scanning actuator 20 is controllable for directing the electron beam 18 at a series of spaced apart points of the crystalline sample 12. In other words, the scanning actuator 20 may control movement of the electron source 16 to move the electron beam 18 relative to the sample 12 on the sample holder 14, or the scanning actuator may control movement of the sample holder relative to the electron beam, or both.

An image processor 24 is provided to process images formed on a phospor screen 22, e.g., by intensifying and/or amplifying the images. The image processor 24 may comprise a low light or charged coupled device (CCD) camera 28 to capture the images. The phospor screen 22 is mounted adjacent the sample holder 14 so that it is parallel to the incident electron beam 18. Diffracted electrons from the sample 12 form images on the phosphor screen 22. These images are known as Kikuchi diffraction patterns and include Kikuchi bands, which can be used to determine the crystallographic grain orientation at a point within a scan area of the sample 12. The pattern center is preferably located near the top of the phosphor screen 22 for maximum band formation.

The image processor 24 mathematically decomposes the Kikuchi diffraction pattern through a Hough transform to identify the band structure, as is well known to those skilled in the art. See, for example, U.S. Pat. No. 6,326,619. The geometrical symmetry of the band structure is used to determine the crystallographic grain orientation of the crystalline sample at the current point. A controller 26 compares the crystallographic grain orientation at the current point with the crystallographic grain orientation from a previous point. The electron beam 18 or the sample holder 14 is then stepped to the next point and the process is repeated. The stepping occurs in a raster pattern with a predetermined step size over the entire scan area.

The crystallographic grain orientation of a crystal phase varies within a narrow tolerance. This tolerance is typically less than the noise exhibited by the Hough transformation conversion to angular spacing between crystal planes. Therefore, only a single determination of the crystallographic grain orientation is needed for each point. In a preferred embodiment, the step size or spacing between sample points is set such that each point is taken from a different grain within a scan area of the crystalline sample 12. The term "step size," as used in the disclosure is the distance between consecutive points of a sample at which the electron beam 18 is directed for grain orientation analysis.

The step size is greater than a "known grain size" of the crystalline sample and/or at least as large as a "known grain size." The term "grain size," as used in this disclosure, refers to that measurement of a grain using techniques known to those skilled in the art, e.g., an intercept method (ASTM Test Method E 112) or planimetric method (ASTM Test Method E-2) or other methods. For a description of such test methods, see Vander Voort, "Committee E-4 and Grain Size Measurements: 75 Years of Progress,"ASTM Standardization News (May, 1991).

The known grain size may be characterized as a standardized grain size for a particular crystal phase of the crystalline and may be obtained from publications listing standardized grain size for various materials. One such publication is *The Journal of Vacuum Science and Technology*. The step size for operation of the present invention is a function of grain size, such as ten times the grain size.

Figure 2:
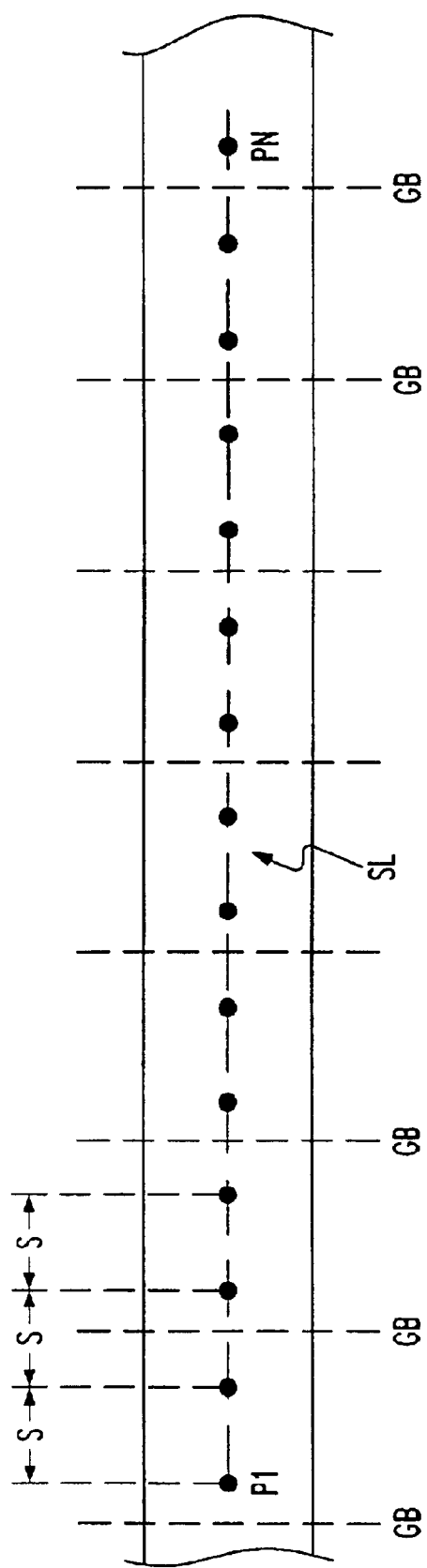
FIG. 2 is a schematic plan view of an example of a scan line according to the prior art.
Figure 3:
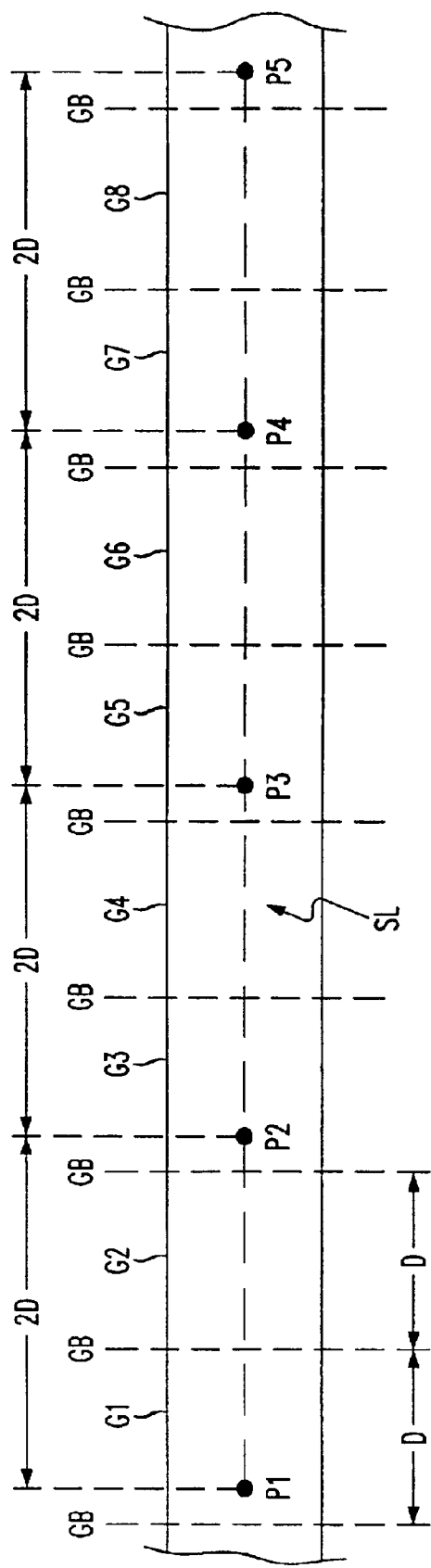
FIG. 3 is a schematic plan view of an example of a scan line according to the present invention.

Referring to FIGS. 2 and 3, example schematic scan lines (SL) of the prior art (FIG. 2) and the present invention (FIG. 3) are now compared. Each of the scan lines depicted in FIGS. 2 and 3 is schematically represented as a straight line. The scan lines disclosed in FIGS. 2 and 3 herein represent a series of spaced apart points taken from a sample and may follow any preselected pattern, or a random pattern. In the present invention, for example, a first point may be randomly selected within a scan area of the sample 12; the next point is spaced apart at a distance that is at least as large as a known grain size of the sample 12. A preselected direction with respect to consecutive points is not critical to the operation of the present invention, but it is preferred to obtain grain orientations of different grains of the sample within a scan area.

The prior art scan line SL of FIG. 2 includes spaced-apart points P1–PN where data is taken. The points P1–PN are spaced apart by a fixed step size S, e.g., 50 nanometers. Grain boundaries (GB) exist within this sample scan line SL and, as illustrated, the number of data points P1–PN is fixed, based on the fixed step size S.

The scan line SL illustrated in FIG 3, according to the present invention, includes spaced apart points P1 through P7 where data is taken. Grain boundaries (GB) exist between grains (G1 through G8), within the sample scan line SL, but the spacing between points is increased to reflect a point taken from a different grain within a scan area of the sample 12. For example, the spacing between each of the points P1 through P5 is twice the size of the grains G1 G8. In this manner, a grain orientation analysis can be taken from a different grain within the scan line for each given point.

Figure 4:
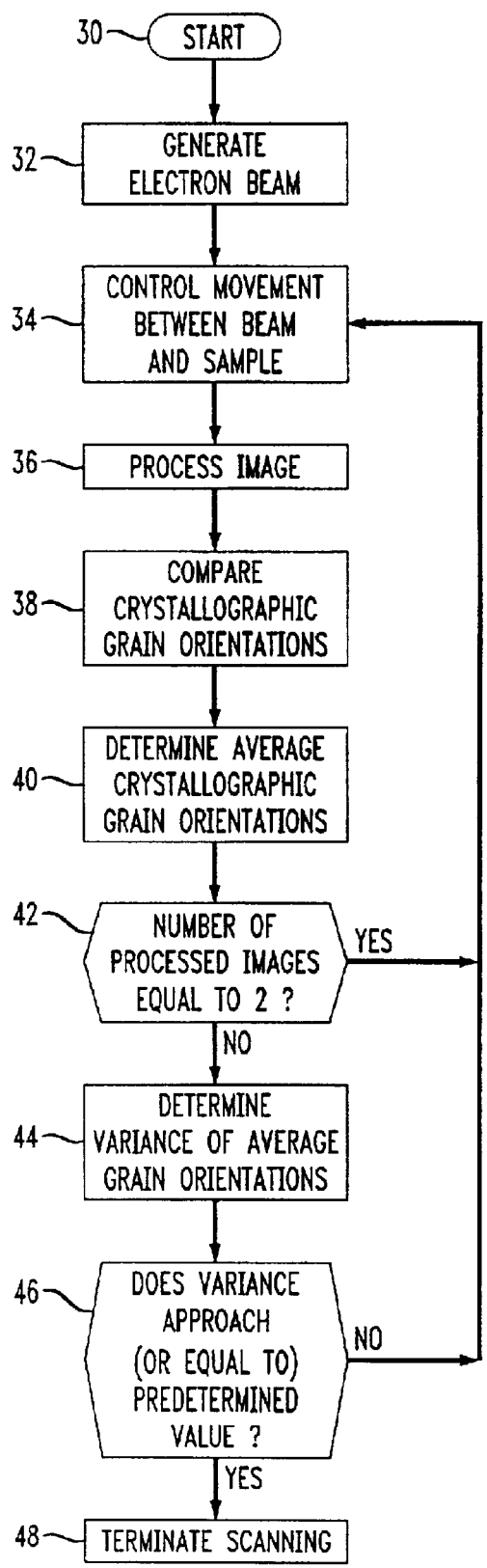
FIG. 4 is a flowchart illustrating the basic steps of a method in accordance with the present invention.

Referring to FIG. 4, the basic steps of the method for scanning a crystalline sample 12 in accordance with the present invention are now described. In accordance with the present invention, the method begins (Block 30) and the sample 12, e.g., a copper film deposited on a semiconductor wafer, is held at a glancing angle to an electron beam 18. For example, the sample 12 may be held by a sample holder 14 or stage, as shown in FIG. 1, in a substantially horizontal position. Preferably, the glancing angle θ is about 20 degrees. At Block 32, an electron beam 18 is generated at the sample 12 and at Block 34, the relative movement between the sample 12 and the Block 34 is controlled to direct the electron beam at a series of spaced apart points of the crystalline sample.

Diffracted-electrons from the crystalline sample 12 define an image, which is processed (Block 36), e.g., by an image processor which preferably includes a low light camera or a CCD camera. The image may be formed on a phosphor screen 22 and comprises a Kikuchi diffraction pattern. The step of processing the image (Block 36) may include converting the Kikuchi diffraction pattern to a Hough space to identify the Kikuchi bands at a current point within the crystalline sample 12. Also, the step of processing the image (Block 36) may include determining a crystallographic grain orientation at the current point within the crystalline sample 12 based on the Kikuchi bands.

The method preferably includes a step (Block 38) of comparing the crystallographic grain orientation from the current point with the crystallographic grain orientation from a previous point. At Block 40, an average grain orientation between the current point and the previous point is determined. For example, with respect to FIG. 2, if the grain orientation of P1 is (1,1,1) and the grain orientation of P2 is (0,0,1), the average grain orientation is the vector that bisects the direction vectors of the (1,1,1) and (0,0,1) planes.

At block 42, if the average grain orientation of only two points has been taken, then the crystallographic grain orientation for a third point must be determined. Once a grain orientation for a third point, P3 (FIG. 3) is taken, it is compared to the grain orientation of points P1 and P2. At Block 40, an average grain orientation for points P1, P2 and P3 is determined to be, for example. In the next step (Block 44), the controller 26 determines a variance between average grain orientation for points P1–P2 and an average grain orientation calculated for points P1, P2 and P3.

At Block 44 a variance between the average grain orientation determined for points P1 and P2 is compared to the average grain orientation for points P1, P2 and P3, to determine a variance in average grain orientation. The term "variance," as used in this disclosure, shall include a variance or standard deviation in average grain orientations, which variance and/or standard deviations are calculated from a statistical analysis of the data comparing grain orientations and/or average grain orientations. The mathematical formulas are well known to those skilled in the art.

In the next step (Block 46), the variance in the average grain orientation of the sample 12 is compared to a predetermined value. If the variance approaches, or is equal to, the predetermined value the scanning is terminated at Block 48. If the variance is not approaching, or equal, to the predetermined value the scanning of the sample 12 continues to the next point. The scanning process is repeated for points P4 and P5. The variance in grain orientation is monitored during the scanning procedure, or until the variance approaches, or is equal to, the predetermined value, at which step (Block 48), the scanning is terminated. Typically, the predetermined value will be zero.

A benefit of the method of the present invention is that is provides faster collection. In accordance with the method, the number of data points within a grain structure can be decreased where points taken at a step size larger than a known grain size of the crystalline sample is needed. An adequate sample of data is collected for evaluation of the crystalline sample, in a minimal amount of time. With respect to fabrication of semiconductor devices, the crystallographic grain orientation of each of respective scan points can be used to calculate a preferred grain orientation of the sample, which calculation is well known to those skilled in the art.

Many modifications and other embodiments of the invention will come to the mind of one skilled in the art of having the benefit of the teachings presented in the foregoing descriptions and the associated drawings. Therefore, it is understood that the invention is not to be limited to the specific embodiments disclosed, and that modification and embodiments are intended to be included within the scope of the appended claims.

What is claimed is:

1. A method for determining an average grain orientation of a crystalline sample, the method comprising the steps of:
   (a) providing a crystalline sample having a known grain size;
   (b) generating an electron beam;
   (c) controlling relative movement between the electron beam and the crystalline sample to direct the electron beam at a series of spaced apart paints within a scanning area of the crystalline sample;
   (d) processing an image based on electron diffraction from the crystalline sample; and
   (e) spacing the points apart a distance that is greater than the know grain size of the crystalline sample to obtain respective images representative of different grains of said crystalline sample.

2. The method of claim 1 wherein said stop of processing an image comprises comparing images representative of different grains within the crystalline sample and monitoring a variance in an average grain orientation of said processed images.

3. The method of claim 2 further comprising the step of terminating the scanning of the crystalline sample as said variance in the average grain orientation approaches a predetermined value.

4. The method of claim 2 wherein said stop of processing an image further comprises determining a crystallographic grain orientation for each said point of said series of points.

5. A method for determining an average grain orientation of a crystalline sample, the method comprising the steps of:
    (a) providing a crystalline sample having a known grain size;
    (b) generating an electron beam;
    (c) controlling relative movement between the electron beam and the crystalline sample to direct the electron beam at a series of spaced apart points within a scanning area of the crystalline sample;
    (d) processing an image based upon electrons diffracted from the crystalline sample;
    (e) determining an average grain orientation for said crystalline sample from said image processing;
    (f) monitoring a variance in the average grain orientation during the scanning of the crystalline sample.

6. The method of claim 5 further comprising the step of terminating the scanning of the crystalline sample as said variance in the average grain orientation approaches a predetermined value.

7. The method of claim 6 wherein said predetermined value is zero.

8. The method of claim 5 further comprising the step of setting a spacing between the points a distance so each said point is representative of a different grain of said crystalline sample.

9. The method of claim 5 further comprising the step of setting a spacing between the points a distance that is greater than the known grain size of said crystalline sample.

10. The method of claim 5 wherein said step of processing an image comprises comparing images representative of different grains of the crystalline sample and determining said average grain orientation of the crystalline sample from said processed images.

11. The method of claim 10 wherein said step of processing an image further comprises determining a crystallographic grain orientation for each said point of said series of points.

12. The method of claim 10 further comprising the step of terminating the scanning as said variance in grain orientation of the crystalline sample approaches a predetermined value.

13. The method of claim 12 wherein said predetermined value is zero.

14. An apparatus for determining an average grain orientation of a crystalline sample, the apparatus comprising:
    (a) a sample holder for holding a crystalline sample having a known grain size;
    (b) an electron source for generating an electron beam;
    (c) a scanning actuator for controlling the relative movement between the electron beam and the crystalline sample, the scanning actuator being controllable for directing the electron beam at a series of spaced apart points of the crystalline sample;
    (d) an image processor for processing an image based upon electron diffraction from the crystalline sample; and
    (e) a controller for controlling the scanning actuator to space said points apart a distance that is greater than the known grain size of the crystalline sample such that each said image is representative of a different grain within the crystalline sample.

15. The apparatus of claim 14 wherein the controller compares a current image with at least one different previously processed image to determine an average grain orientation of said current image and previously processed image.

16. The apparatus of claim 15 wherein the controller determines a variance in the average grain orientation of any processed images including the current image and the at least one previously processed image.

17. The apparatus of claim 16 wherein the controller terminates the scanning when said variance in grain orientation approaches a predetermined value.

* * * * *